United States Patent [19]
Hishii

[11] Patent Number: 5,086,777
[45] Date of Patent: Feb. 11, 1992

[54] SMALL-SIZED DISPOSABLE PRESSURE TRANSDUCER APPARATUS WITH A TEMPERATURE COMPENSATING CIRCUIT DISPOSED ADJACENT A PASSAGEWAY COUPLED WITH A CATHETER

[75] Inventor: Toshiyasu Hishii, Tokyo, Japan

[73] Assignee: NEC Corporation, Tokyo, Japan

[21] Appl. No.: 517,882

[22] Filed: May 2, 1990

[30] Foreign Application Priority Data

May 2, 1989 [JP] Japan .................................. 1-113213

[51] Int. Cl.$^5$ ................................................ A61B 5/02
[52] U.S. Cl. ..................... 128/675; 128/637; 73/4 R; 73/708; 73/754
[58] Field of Search ............... 73/4 R, 763, 766, 708, 73/754; 128/670, 672, 673-675, 637, 645

[56] References Cited

U.S. PATENT DOCUMENTS

| | | | |
|---|---|---|---|
| 4,576,181 | 3/1986 | Wallace et al. | 128/675 |
| 4,586,382 | 5/1986 | Sinha | 73/708 |
| 4,658,651 | 4/1987 | Le | 73/708 |
| 4,825,876 | 5/1989 | Beard | 128/675 |

Primary Examiner—Max Hindenburg
Assistant Examiner—Robin R. Longo
Attorney, Agent, or Firm—Sughrue, Mion, Zinn, Macpeak & Seas

[57] ABSTRACT

A blood pressure transducer apparatus having a semiconductor pressure sensor and a temperature compensating circuit mounted on a substrate which is fixedly mounted on a wall portion of a housing, with a fluid passageway being formed in the wall portion to be coupled with a fluid-filled catheter inserted into a blood vessel and being hydraulically coupled with the sensor. In order to improvement of temperature compensation, manufacturing yield and reliability as well as small-sizing the apparatus, the substrate has a first surface on which the sensor is mounted and an opposite second surface. The second surface is fixed at a partial area thereof to an abutment on an inner surface of the wall portion. The temperature compensating circuit is formed on the remaining area of the second surface so that the temperature compensating circuit is adjacent to the passageway.

4 Claims, 4 Drawing Sheets

SMALL-SIZED DISPOSABLE PRESSURE TRANSDUCER APPARATUS WITH A TEMPERATURE COMPENSATING CIRCUIT DISPOSED ADJACENT A PASSAGEWAY COUPLED WITH A CATHETER

BACKGROUND OF THE INVENTION

1. Field of the Invention

The present invention relates to a disposable pressure transducer apparatus for use in blood pressure measurement, and in particular, to such an apparatus comprising a semiconductor pressure transducer element or a semiconductor pressure sensor hydraulically coupled to a housing passageway and a temperature compensating circuit connected to the semiconductor pressure sensor.

2. Description of the Prior Art

In the pressure transducer apparatus, the semiconductor pressure sensor converts blood pressure pulses transmitted through a fluid in a catheter inserted into a blood vessel into an electric signal. The electric signal is temperature compensated by the temperature compensating circuit and is transmitted to a monitoring device which displays the blood pressure.

A known apparatus of a type described above comprises a housing having an interior and a wall portion formed with the housing passageway to be coupled with the catheter. The semiconductor pressure sensor and an electric circuit including the temperature compensating circuit are mounted on a first surface of a dielectric substrate. The substrate has an opposite or second surface which is secured onto an inner surface of the wall portion. The semiconductor pressure sensor is hydraulically coupled with the housing passageway through the wall portion. The electric circuit is connected to the semiconductor pressure sensor and electric conductors electrically connect the electric circuit to the monitoring device. The known apparatus is disclosed in U.S. Pat. No. 4,576,181 issued to Wallace et al and assigned to Utah Medical Products (Reference I).

Since the semiconductor pressure sensor and the electric circuit including the temperature compensating circuit are formed on the same first surface of the substrate together with an opaque cap or a chip cover for the sensor in the known apparatus, manufacture and assembly of the apparatus are greatly facilitated as described in Reference I.

However, in the known apparatus the temperature compensation is not very good because the temperature compensating circuit is disposed on the first surface of the substrate away from the wall portion having the passageway and is remote from the fluid introduced into the passageway.

The temperature compensating circuit is usually formed on the substrate by a thick printing technique. That is, resistor and conductor patterns are formed by the printing method. The resistors are trimmed by a laser working technique to adjust the resistances. Evaporation and/or dust of the resistors is generated in the laser trimming process and contaminates an outer surface of the semiconductor pressure sensor mounted on the same surface of the substrate. This is not avoided by provision of the chip cover because the chip cover is provided with an aperture for communicating the semiconductor pressure sensor with the atmosphere. As a result, the semiconductor pressure sensor is deteriorated in reliability so that the apparatus has a problem in manufacturing yield and reliability of operation.

In order to form the electric circuit including the temperature compensating circuit on the same surface of the substrate on which the semiconductor pressure sensor is mounted together with the chip cover, the substrate is required comparatively large in size. This unfortunately results into a large size of the apparatus.

SUMMARY OF THE INVENTION

It is an object of the present invention to provide a disposable pressure transducer apparatus which is excellent in temperature compensation, manufacturing yield, and reliability and which is small in size.

The present invention is applicable to a disposable pressure transducer apparatus for use in blood pressure measurement. The apparatus comprises a housing having an interior and a wall portion in which a passageway is formed to be coupled with a catheter, the passageway being introduced a fluid through the catheter inserted into a blood vessel, a dielectric substrate having a first surface and an opposite second surface, the substrate being fixedly mounted in the interior of the housing with the second surface being onto an inner surface of the wall portion, a semiconductor pressure sensor mounted on the first surface of the substrate and hydraulically coupled with the passageway, and an electric circuit including a temperature compensating circuit means and being mounted on the substrate, the electric circuit being electrically connected to the semiconductor pressure sensor and to electric conductive means for electrically connecting the electric circuit with a monitoring device.

According to the present invention, the temperature compensating circuit is formed on the second surface of the substrate so that the temperature compensating circuit is positioned adjacent the passageway through the wall portion.

The first surface of the substrate has a first specific area on which the semiconductor pressure sensor is mounted and a remaining area as a first particular area. The second surface has a second specific area corresponding to the first specific area and a remaining area as a second particular area. The temperature compensating circuit is formed on the second particular area. The wall portion is provided with an abutment slightly projecting from the inner surface, and the substrate is fixed at the second specific area onto the abutment.

The electric circuit comprises a circuit portion connecting with the semiconductor pressure sensor and the electric conductive means, and the circuit portion is formed on the first particular area in the first surface of the substrate.

The substrate is formed with through-holes extending therethrough from the first particular area to the second particular area by which the temperature compensating circuit is electrically coupled with the circuit portion.

DESCRIPTION OF PREFERRED EMBODIMENT

Figure 1:
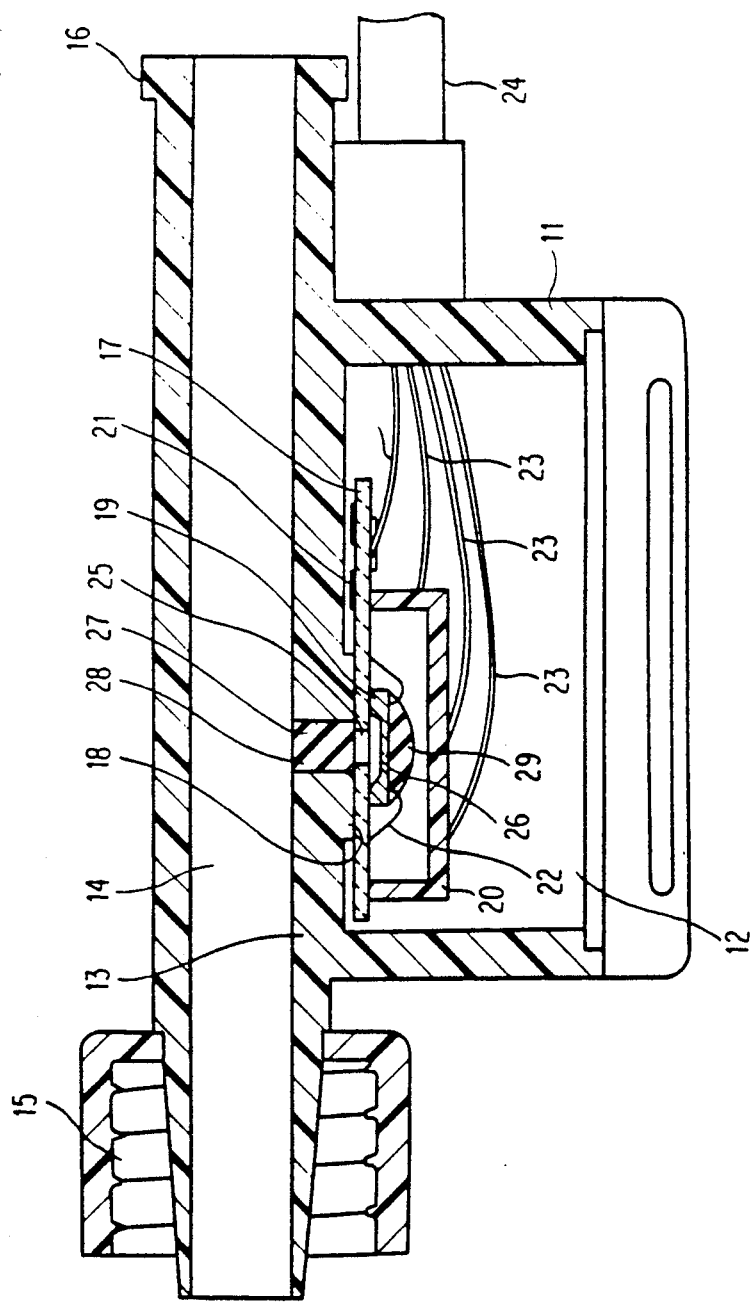
FIG. 1 is a sectional view of a disposable pressure transducer apparatus according to an embodiment of the present invention.

Referring to FIG. 1, the disposable pressure transducer apparatus 10 according to an embodiment shown therein comprises a housing 11. The housing 11 is provided with an interior 12 defined by a wall. A portion 13 of the wall is formed with a fluid passageway 14. The passageway 14 is provided with a mechanical connectors 15 and 16 at opposite ends for mechanically connecting with a catheter (not shown) which is inserted into a blood vessel. The mechanical connectors 15 and 16 are, for example, a lower female connector and a male connector, as shown in the figure.

The passageway 14 is introduced a fluid flowing through the catheter.

A dielectric substrate 17 is fixedly mounted in the interior 12 of the housing 11. The substrate 17 has a first surface and a second surface and is fixedly mounted at the second surface onto an inner surface of the wall portion 13.

In detail, the first surface has a first specific area and the remaining area is denoted as a first particular area, and the second surface of the substrate has a second specific area corresponding to the first specific area and the remaining area corresponding to the first particular area is denoted as a second particular area. The wall portion 13 is provided with an abutment 18 slightly and partially projecting from the inner surface. The substrate 17 is fixed onto the abutment 18 so that the second specific area comes into contact with the abutment 18.

A semiconductor pressure sensor 19 is mounted on the first specific area of the first surface of the substrate 17 and is covered with an opaque chip cover 20 which is also mounted on the first surface. An electric circuit is also mounted or formed on the substrate 17 and is electrically connected to the semiconductor pressure sensor 19.

The electric circuit comprises a temperature compensating circuit 21 formed on the second particular area of the second surface of the substrate 17. A circuit pattern is also formed on the first particular area of the first surface of the substrate 17 as a portion of the electric circuit. The circuit pattern comprises a portion which is electrically connected with the semiconductor pressure sensor 19 through bonding wires 22 and another portion which is electrically connected with conductors 23 for electrically connecting with a monitoring device (not shown). The conductors 23 are collected and are led out of the housing 11 as an electric cable 24. The circuit pattern is also electrically connected with the temperature compensating circuit 21 through through-holes formed in the substrate 17. The circuit pattern will later be described in detail.

The substrate 17 is formed with a first hole 25 facing a diaphragm 26 of the semiconductor pressure sensor 19 mounted on the first surface of the substrate 17. The wall portion 13 is also provided with a second hole 27 communicating the passageway 14 with the first hole 25. Accordingly, the diaphragm 26 is hydraulically coupled with the passageway 14. As a result, the fluid pressure in the passageway 14 is transmitted to the diaphragm 26 of the semiconductor pressure sensor 19 through the first and the second holes 25 and 27. A gel material 28 of silicone is loaded in the first hole 25 and/or the second hole 27 so as to prevent the fluid from direct contact with the diaphragm 26.

A top surface of the semiconductor pressure sensor 19 is covered with a silicone gel 29 for protecting the top surface and the bonding wires 22.

The fluid pressure transmitted to the diaphragm 26 through the first and the second holes 25 and 27 is converted into an electric signal by the semiconductor pressure sensor 19. The signal is temperature compensated by the temperature compensating circuit 21 and thereafter transferred through the conductors 23 and the electric cable 24 to the monitoring device.

In the arrangement, since the substrate 17 is fixed onto the abutment 18 at the second specific area of the second surface and the temperature compensating circuit 21 is disposed on the second particular area of the second surface, the temperature compensating circuit 17 is positioned to face the wall portion 14 through a small gap and is therefore located adjacent the passageway 14 so that the pressure can be measured under reliable temperature compensation. Furthermore, the semiconductor pressure sensor 19 is mounted on a surface of the substrate 17 opposite the temperature compensating circuit 21, so that the semiconductor pressure sensor 19 can be protected from the evapolation and/or dust generated in laser-trimming of resistors of the temperature compensating circuit 21. Moreover, the substrate of a reduced area can be used in comparison with a known device where the semiconductor pressure sensor and the temperature compensating circuit are mounted on the same surface of the substrate.

Figure 2:
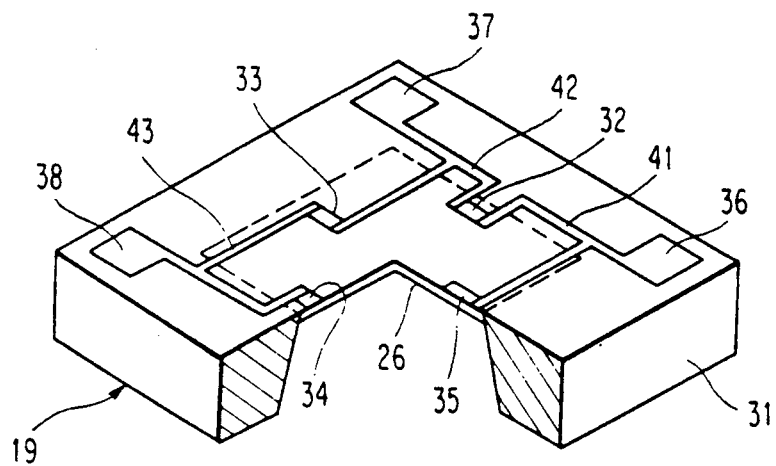
FIG. 2 is a partially exploded perspective view of a semiconductor pressure sensor used in the apparatus in FIG. 1.
Figure 3:
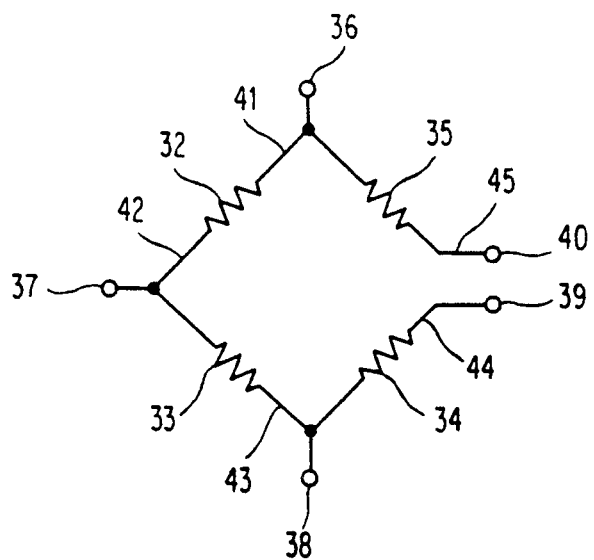
FIG. 3 is an equivalent electric circuit of the semiconductor pressure sensor of FIG. 2.

Referring to FIG. 2, the semiconductor pressure sensor 19 comprises a die 31 of a silicon semiconductor element and the diaphragm 26 of a thin film formed at a center of the die 31. Four diffused resistors 32 through 35 are formed at different spaced positions on the diaphragm 26. Five pads of aluminum 36 through 40 (39 and 40 are shown in not FIG. 2 but FIG. 3) are formed on the die 31 and are connected with the diffused resistors 32 through 35 by conductive leads 41 through 45 (44 and 45 are shown in not FIG. 2 but FIG. 3) of aluminum to form a Wheatstone bridge circuit as shown in FIG. 3.

In the semiconductor pressure sensor 19, when a pressure is applied to the diaphragm 26, resistances of the diffused resistors 32 through 35 vary by the piezoresistive effect. Thus, the pressure is converted into an electric signal.

Figure 4:
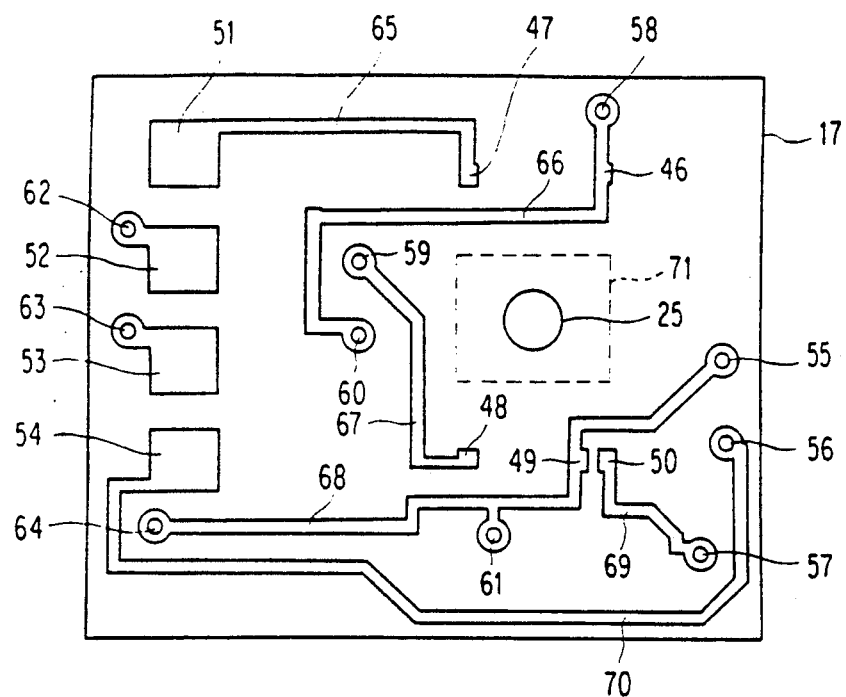
FIG. 4 is a plan view of a substrate for mounting the semiconductor pressure sensor thereon, illustrating a circuit pattern formed thereon.

Referring to FIG. 4, a electric circuit pattern is shown which is formed on the first particular area of the first surface of the substrate 17. The circuit pattern comprises stitch lands 46 through 50 which are electrically connected with the pads 36 through 40 of the semiconductor pressure sensor 19 through bonding wires (22 in FIG. 1). The circuit pattern further comprises terminal pads 51 through 54 which are connected to conductors 23 in FIG. 1. The substrate 17 is also provided with through-holes 55 through 64 extending from the first surface to the second surface of the substrate 17 so as to electrically connect the circuit pattern on the first surface with the temperature compensating circuit 21 on the second surface. The circuit pattern further comprises leads 65–70 of a predetermined pattern which connect the stitch lands 46 through 50, the pads 51 through 54 and through-holes 55 through 64 with one another according to a predetermined circuit pattern.

In FIG. 4, an area enclosed by a dotted line 71 is the first specific area on which the semiconductor pressure sensor 19 is mounted and fixed with a silicone adhesive agent. The hole 25 is formed at a center of the first specific area 71. The circuit pattern is formed on the remaining area as the first particular area on the first surface. The chip cover (20 in FIG. 1) is also fixedly mounted on the first surface after completion of connecting the pressure sensor with the stitch lands 46 through 50 by bonding wires.

Figure 5:
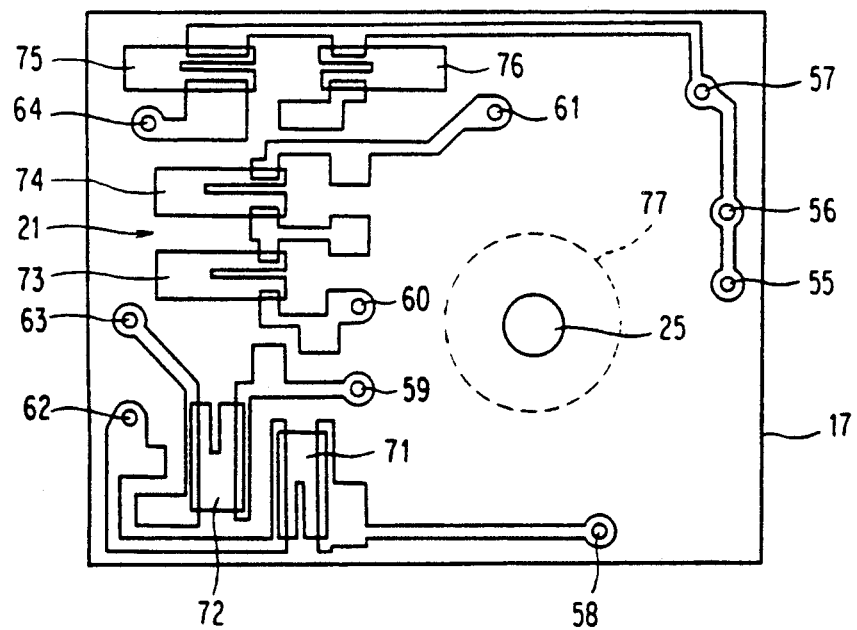
FIG. 5 is a bottom view of the substrate, illustrating a circuit pattern of a temperature compensating circuit formed thereon.

Referring to FIG. 5, the second surface of the substrate 17 is provided with the temperature compensating circuit 21 formed on the second particular area. The temperature compensating circuit 21 comprises thick film resistors 71 through 76 and leads which connect those resistors 71 through 76 and the through-holes 55 through 64 with one another according to a predetermined circuit pattern. Thus, the electric circuit including the semiconductor pressure sensor 19 and the temperature compensating circuit 21 has an electric equivalent circuit shown in FIG. 6.

Figure 6:
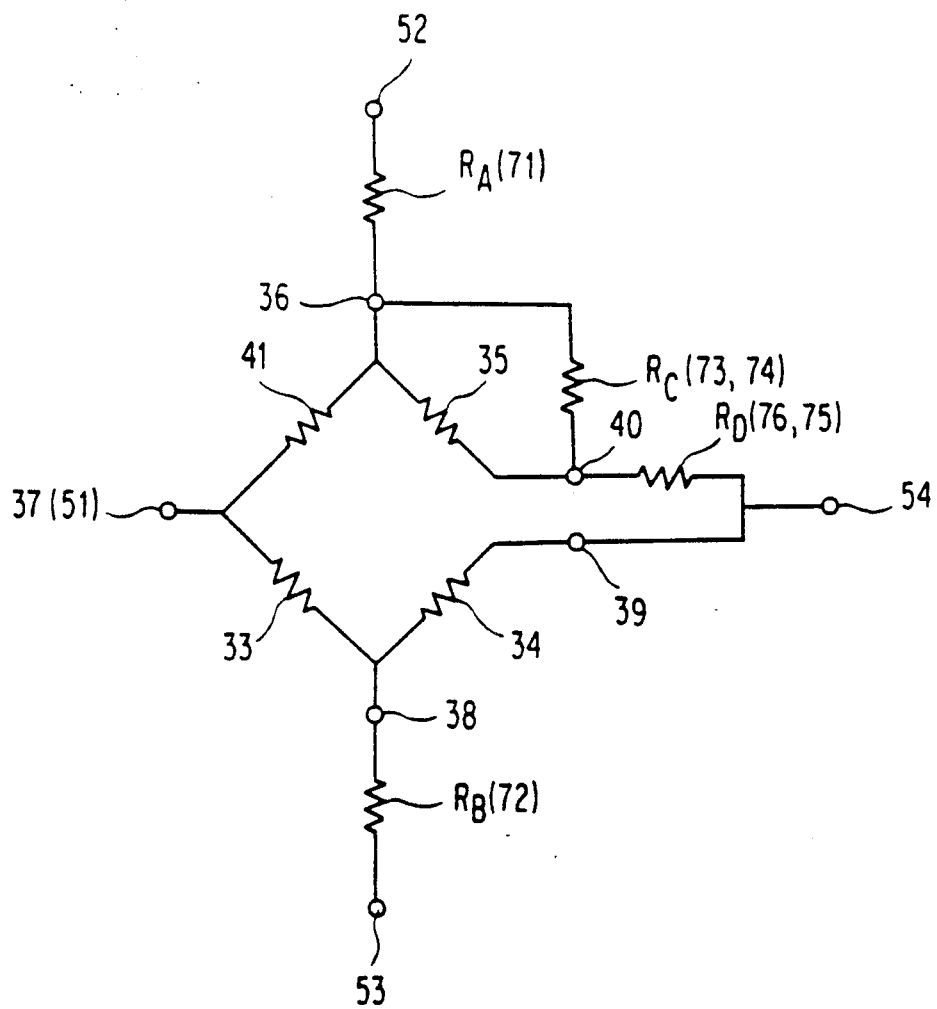
FIG. 6 is an equivalent electric circuit of the disposable pressure transducer apparatus.

In FIG. 6, resistances RA and RB are provided by resistors 71 and 72, respectively, and are determined so as to adjust sensitivity of the semiconductor pressure sensor 19. A resistance RC is determined by the resistors 73 and 74 and the other resistance RD is given by resistors 76 and 75. Those resistances RC and RD are determined to adjust the offset voltage of the semiconductor pressure sensor 19 and to reduce the temperature response of the offset voltage.

Returning to FIG. 5, the second surface of the substrate 17 is provided with the second specific area enclosed by a dotted line 77 and the remaining area as the second particular area. The second specific area is corresponding to the first specific area and is provided with the hole 25 at a center portion. The second specific area of the substrate 17 is fixed to and tightly sealed with the abutment 18 on the inner wall portion 13 (FIG. 1) to fixedly mount the substrate 17 to the wall portion 13.

The temperature compensating circuit 21 is formed on the second particular area in the second surface of the substrate 17.

What is claimed is:

1. In a disposable pressure transducer apparatus for use in blood pressure measurement, said apparatus comprising a housing having an interior and a wall portion in which a passageway is formed to be coupled with a catheter, said passageway being for introduction of a fluid through said catheter inserted into a blood vessel, a dielectric substrate having a first surface and an opposite second surface, said substrate being fixedly mounted in said interior of the housing with said second surface being onto an inner surface of said wall portion, a semiconductor pressure sensor mounted on said first surface of said substrate and hydraulically coupled with said passageway, and an electric circuit including a temperature compensating circuit and being mounted on said substrate, said electric circuit being electrically connected to said semiconductor pressure sensor and to electric conductive means for electrically connecting said electric circuit with a monitoring device, the improvement wherein said first surface of said substrate has a first specific area on which said semiconductor pressure sensor is mounted and the remaining area as a first particular area, said second surface has a second specific area corresponding to said first specific area and the remaining area has a second particular area, said temperature compensating circuit is formed on said second particular area, said wall portion is provided with an abutment slightly projecting from said inner surface, and said substrate is fixed at said second specific area onto said abutment so that said temperature compensating circuit on said second particular area is positioned to face said inner surface of said wall portion with a small gap.

2. A disposable pressure transducer apparatus as claimed in claim 1, wherein said electric circuit mounted on said substrate includes a circuit portion connecting with said semiconductor pressure sensor and said electric conductive means, said circuit portion being formed on said first particular area of said first surface of said substrate.

3. A disposable pressure transducer apparatus as claimed in claim 2, wherein said substrate is formed with through-holes extending therethrough from said first particular area to said second particular area by which said temperature compensating circuit is electrically coupled with said circuit portion.

4. A disposable pressure transducer apparatus as claimed in claim 1, wherein said substrate is formed with a first hole in said first specific area, said first hole opening in said second specific area, said wall portion is formed with a second hole in said abutment, said second hole opening into said passageway, said first and said second holes being registered with each other to form a communication hole for hydraulically coupling said semiconductor pressure sensor with said passageway, and a gel is loaded within said communication hole for preventing said fluid in said passageway from direct contact with said semiconductor pressure sensor through said communication hole.

* * * * *